(12) United States Patent
Hagiya et al.

(10) Patent No.: US 7,282,609 B2
(45) Date of Patent: Oct. 16, 2007

(54) PROCESS FOR PRODUCTION OF 1-ARYL-5-(TRIFLUOROMETHYL)-1H-TETRAZOLES

(75) Inventors: Kazutake Hagiya, Takasago (JP); Yasuhiro Sato, Takasago (JP); Kiyoto Koguro, Takasago (JP); Sunao Mitsui, Takasago (JP)

(73) Assignee: Toyo Kasei Kogyo Company Limited, Osaka (JP)

( * ) Notice: Subject to any disclaimer, the term of this patent is extended or adjusted under 35 U.S.C. 154(b) by 0 days.

(21) Appl. No.: 10/573,034

(22) PCT Filed: Sep. 30, 2004

(86) PCT No.: PCT/JP2004/014781

§ 371 (c)(1),
(2), (4) Date: Mar. 22, 2006

(87) PCT Pub. No.: WO2005/035484

PCT Pub. Date: Apr. 21, 2005

(65) Prior Publication Data

US 2007/0106080 A1    May 10, 2007

(30) Foreign Application Priority Data

Oct. 10, 2003  (JP) .............................. 2003-385936
Apr. 3, 2004  (JP) .............................. 2004-136859

(51) Int. Cl.
*C07C 249/00* (2006.01)
*C07D 257/04* (2006.01)
(52) U.S. Cl. ....................................... 564/271; 548/250
(58) Field of Classification Search .................... None
See application file for complete search history.

(56) References Cited

U.S. PATENT DOCUMENTS 4,299,831 A    11/1981    Clémence et al. ........... 424/251

FOREIGN PATENT DOCUMENTS

| JP | 40-13726 B1 | 7/1965 |
| JP | 46-10526 B1 | 3/1971 |
| JP | 63-112570 A | 5/1988 |
| JP | 4-243855 A | 8/1992 |
| JP | 5-286972 A | 11/1993 |
| JP | 9-309883 A | 12/1997 |
| JP | 2001-172248 A | 6/2001 |
| JP | 2002-284770 A | 10/2002 |
| JP | 2003-321431 A | 11/2003 |

OTHER PUBLICATIONS

Smith, Peter A.S. et al., "The Thermal Breakdown of Diaryltetrazoles", *J. Am. Chem. Soc.*, vol. 80, pp. 4647-4654, 1958.
Vaughan, John et al., "The Effect of Some Substituents on the Thermal Breakdown of Diaryltetrazoles", *J. Org. Chem.*, vol. 23, pp. 1909-1912, 1958.
Kadaba, Pankaja K., "Protic-Dipolar Aprotic Solvents in 1,3-Cycloaddition Reactions." *Synth. Commun.*, vol. 1, pp. 1-5, 1971.
Padwa, Albert et al., "Synthetic Approaches Toward the Bi (2H-azirine) System", *J. Org. Chem.*, vol. 44, No. 19, pp. 3281-3287, 1979.
Xiao, Jingbo et al., "Synthesis of Trifluoromethyltetrazoles Via Building Block Strategy", *J. Fluorine Chem.*, vol. 99, pp. 83-85, 1999.
Tamura, Kenji et al., "One-Pot Synthesis of Trifluoroacetimidoyl Halides", *J. Org. Chem.*, vol. 58, pp. 32-35, 1993.
Shchegel'skii, V.F. et al., "Synthesis and Anticholinesterase Activity of Flourine-Containing Aryliminophosphonates and Phosphinates", *Pharmaceutical Chemistry Journal*, 30(11), pp. 690-692, 1996.
Xiao, Jingbo et al., "Synthesis of Trifluoromethyltetrazoles via Building Block Strategy", *Journal of Fluorine Chemistry*, 99(1), pp. 83-85, 1999.

*Primary Examiner*—Samuel Barts
(74) *Attorney, Agent, or Firm*—Kubovcik & Kubovcik

(57) ABSTRACT

The present invention relates to a process for producing an N-aryl-2,2,2-trifluoroacetimidoyl chloride represented by Formula (2):

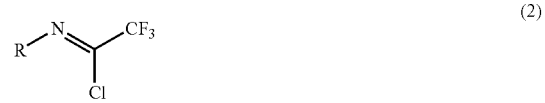

the process comprising the step of reacting in an organic solvent a tertiary amine, a 2,2,2-trifluoro-N-arylacetamide represented by Formula (1):

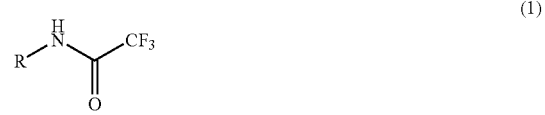

and at least one member selected from the group consisting of phosphorus oxychloride and diphenyl chlorophosphate; and a process for producing a 1-aryl-5-(trifluoromethyl)-1H-tetrazole represented by Formula (4):

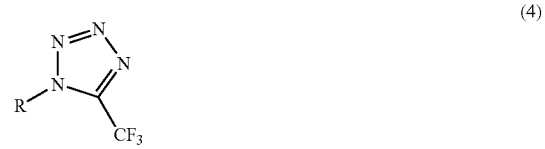

the process comprising the step of reacting in an aromatic hydrocarbon solvent, in the presence of an amine salt, an N-aryl-2,2,2-trifluoroacetimidoyl chloride represented by Formula (2) shown above and an azide.

8 Claims, No Drawings

PROCESS FOR PRODUCTION OF 1-ARYL-5-(TRIFLUOROMETHYL)-1H-TETRAZOLES

TECHNICAL FIELD

The present invention relates to processes for producing 1-aryl-5-(trifluoromethyl)-1H-tetrazoles and their production intermediates, i.e., N-aryl-2,2,2-trifluoroacetimidoyl chlorides. 1-Aryl-5-(trifluoromethyl)-1H-tetrazoles are important intermediates for a variety of pharmaceuticals.

BACKGROUND ART

A known method for producing a tetrazole compound is blowing hydrogen azide gas into an imidoyl chloride compound at 200° C. or higher (*J. Am. Chem. Soc.*, vol. 80, 1958, p. 4647). Other known methods include a reaction using sodium azide in an aqueous solvent (*J. Org. Chem.*, vol. 23, 1958, p. 1909); reaction using an aprotic polar solvent such as DMF, acetonitrile or the like (*Synth. Commun.*, vol. 1, 1971, p. 1; *J. Org. Chem.*, vol. 19, 1979, p. 3281; *J. Fluorine Chem.*, vol. 99, 1999, p. 83); and like methods.

However, the method in which hydrogen azide gas is blown at 200° C. or higher may allow toxic hydrogen azide to escape the reaction system, and thus poses great safety risks for industrial scale production. In reactions using a solvent such as DMF, acetonitrile or the like, sodium azide may react with the solvent when heating is necessary. Moreover, since such solvents are water-miscible, large amounts of the reaction product dissolves in the aqueous phase in the post-treatment. Furthermore, when DMF or a like high-boiling-point solvent is used, solvent removal is difficult if the reaction product is liquid. Therefore, these prior-art production processes are not industrially advantageous.

An example of a conventional production process for an imidoyl chloride compound is converting an amide compound into an imidoyl chloride compound using phosphorus oxychloride, phosphorus pentachloride, thionyl chloride or a like chlorinating reagent. However, when an amide compound having a highly electron withdrawing group such as a trifluoromethyl group is used in this method, the reaction progresses extremely slowly, thereby hindering the efficient production of the imidoyl chloride compound.

*J. Org. Chem.*, vol. 58, 1993, p. 32 teaches a process for efficiently producing an imidoyl chloride compound containing a strongly electron withdrawing trifluoromethyl group using a large excess of carbon tetrachloride as a chlorinating reagent. However, this process is environmentally problematic since carbon tetrachloride is highly toxic and is a regulated substance due to its ozone depletion potential.

A known production process that does not use carbon tetrachloride is one that uses ethyl trichloroacetate. This process produces, for example, N-(4-methoxyphenyl)-2,2,2-trifluoroacetimidoyl chloride in a yield of 76% (Japanese Unexamined Patent Publication No. 2003-321431). This method, however, produces solid triphenylphosphine oxide in a weight-based amount twice or more than that of the desired product, and the removal thereof is difficult. Moreover, since the yield is only 76%, this is not an industrially advantageous process.

DISCLOSURE OF THE INVENTION

An object of the present invention is to provide processes for safely and efficiently producing 1-aryl-5-(trifluoromethyl)-1H-tetrazoles and their production intermediates, i.e., N-aryl-2,2,2-trifluoroacetimidoyl chlorides.

Other objects and characteristics of the present invention will become evident by the disclosure provided below.

The inventors conducted extensive research to achieve the object described above, and found that a 1-aryl-5-(trifluoromethyl)-1H-tetrazole can be safely and efficiently produced by subjecting an N-aryl-2,2,2-trifluoroacetimidoyl chloride and an azide to a reaction in the presence of an amine salt in an aromatic hydrocarbon solvent, and the inventors thus partially accomplished the present invention. Furthermore, the inventors found that an N-aryl-2,2,2-trifluoroacetimidoyl chloride can be safely and efficiently produced by subjecting a 2,2,2-trifluoro-N-arylacetamide, a tertiary amine and at least one member selected from the group consisting of phosphorus oxychloride and diphenyl chlorophosphate to a reaction in an organic solvent, and the inventors thereby accomplished the present invention.

In particular, the present invention provides processes for safely and efficiently producing 1-aryl-5-(trifluoromethyl)-1H-tetrazoles and their production intermediates, i.e., N-aryl-2,2,2-trifluoroacetimidoyl chlorides, as described below.

1. A process for producing an N-aryl-2,2,2-trifluoroacetimidoyl chloride represented by Formula (2):

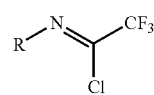

(2)

wherein R is an aryl group optionally having one substituent, the process comprising the step of reacting in an organic solvent a tertiary amine, a 2,2,2-trifluoro-N-arylacetamide represented by Formula (1):

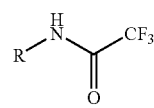

(1)

wherein R is as defined above, and at least one member selected from the group consisting of phosphorus oxychloride and diphenyl chlorophosphate.

2. The process according to Item 1, wherein R is a phenyl, methylphenyl, methoxyphenyl, fluorophenyl, chlorophenyl, bromophenyl, iodophenyl, or naphthyl group.

3. The process according to Item 1 or 2, wherein the tertiary amine is triethylamine.

4. A process for producing a 1-aryl-5-(trifluoromethyl)-1H-tetrazole represented by Formula (4):

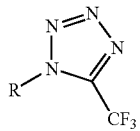

(4)

wherein R is an aryl group optionally having one substituent, the process comprising the step of reacting in an aromatic hydrocarbon solvent, in the presence of an amine salt, an N-aryl-2,2,2-trifluoroacetimidoyl chloride represented by Formula (2):

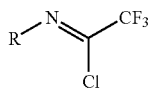

(2)

wherein R is as defined above, and an azide represented by Formula (3):

$$M(N_3)_n$$ (3)

wherein M is an alkali metal or alkaline-earth metal, and n is 1 or 2.

5. The process according to Item 4, wherein R is a phenyl, methylphenyl, methoxyphenyl, fluorophenyl, chlorophenyl, bromophenyl, iodophenyl, or naphthyl group.

6. The process according to Item 4 or 5, wherein the azide is sodium azide.

7. The process according to any one of Items 4 to 6, wherein the amine salt is triethylamine hydrochloride.

8. The process according to any one of Items 4 to 7, wherein the aromatic hydrocarbon solvent is at least one member selected from the group consisting of toluene and xylene.

The process for producing an N-aryl-2,2,2-trifluoroacetimidoyl chloride and the process for producing a 1-aryl-5-(trifluoromethyl)-1H-tetrazole are described below in detail.

[Production of N-aryl-2,2,2-trifluoroacetimidoyl chlorides]

An N-aryl-2,2,2-trifluoroacetimidoyl chloride represented by Formula (2) can be produced by reacting a 2,2,2-trifluoro-N-arylacetamide represented by Formula (1), a tertiary amine, and at least one member selected from the group consisting of phosphorus oxychloride and diphenyl chlorophosphate in an organic solvent.

"R" in Formulae (1) and (2) is an aryl group optionally having one substituent, and preferably a phenyl or naphthyl group optionally having one substituent. The naphthyl group may be either 1-naphthyl or 2-naphthyl. The position of the substituent is not limited. Examples of the substituent are alkyl groups, alkoxy groups, and halogen atoms.

Such alkyl groups may be linear or branched. When branched, the number and position(s) of branch(es) are not limited. For the reaction to progress smoothly, such an alkyl group preferably has 1 to 10 carbon atoms, and more preferably 1 to 4 carbon atoms. Preferable and specific examples are methyl, ethyl, propyl, isopropyl, n-butyl, isobutyl, s-butyl, t-butyl, and like groups.

The alkyl moiety of such an alkoxy group may be linear or branched. When branched, the number and position(s) of branch(es) are not limited. For the reaction to progress smoothly, the alkyl moiety preferably has 1 to 10 carbon atoms, and more preferably 1 to 4 carbon atoms. Preferable and specific examples of such alkoxy groups are methoxy, ethoxy, n-propoxy, isopropoxy, n-butoxy, but-2-oxy, 2-methylprop-1-oxy, 2-methylprop-2-oxy, and like groups.

Such halogen atoms may be fluorine, chlorine, bromine, or iodine.

Particularly preferable examples of R in Formulae (1) and (2) are phenyl, methylphenyl, methoxyphenyl, fluorophenyl, chlorophenyl, bromophenyl, iodophenyl, and naphthyl groups.

In the present invention, 2,2,2-trifluoro-N-arylacetamides may be prepared according to any process. Preferable and specific examples are 2,2,2-trifluoro-N-phenylacetamide, 2,2,2-trifluoro-N-(2-methylphenyl)acetamide, 2,2,2-trifluoro-N-(3-methylphenyl)acetamide, 2,2,2-trifluoro-N-(4-methylphenyl)acetamide, 2,2,2-trifluoro-N-(2-methoxyphenyl)acetamide, 2,2,2-trifluoro-N-(3-methoxyphenyl)acetamide, 2,2,2-trifluoro-N-(4-methoxyphenyl)acetamide, 2,2,2-trifluoro-N-(2-fluorophenyl)acetamide, 2,2,2-trifluoro-N-(3-fluorophenyl)acetamide, 2,2,2-trifluoro-N-(4-fluorophenyl)acetamide, 2,2,2-trifluoro-N-(2-chlorophenyl)acetamide, 2,2,2-trifluoro-N-(3-chlorophenyl)acetamide, 2,2,2-trifluoro-N-(4-chlorophenyl)acetamide, 2,2,2-trifluoro-N-(2-bromophenyl)acetamide, 2,2,2-trifluoro-N-(3-bromophenyl)acetamide, 2,2,2-trifluoro-N-(4-bromophenyl)acetamide, 2,2,2-trifluoro-N-(2-iodophenyl)acetamide, 2,2,2-trifluoro-N-(3-iodophenyl)acetamide, 2,2,2-trifluoro-N-(4-iodophenyl)acetamide, 2,2,2-trifluoro-N-(naphthalen-1-yl)acetamide, and 2,2,2-trifluoro-N-(naphthalen-2-yl)acetamide.

The amount of phosphorus oxychloride used in the present invention is preferably 0.6 to 3.0 mol, and more preferably 0.7 to 2.0 mol, per mol of 2,2,2-trifluoro-N-arylacetamide. The amount of diphenyl chlorophosphate is preferably 1.0 to 3.0 mol, and more preferably 1.5 to 2.5 mol, per mol of 2,2,2-trifluoro-N-arylacetamide. Phosphorus oxychloride and diphenyl chlorophosphate may be used either singly or in combination.

Tertiary amines usable in the present invention are not limited. Preferable and specific examples are trimethylamine, triethylamine, tripropylamine, diisopropylethylamine, tributylamine, tripentylamine, triamylamine, trihexylamine, trioctylamine, triallylamine, pyridine, 2-methylpyridine, 3-methylpyridine, 4-methylpyridine, N-methylmorpholine, N,N-dimethylcyclohexylamine, N,N-dimethylaniline, N,N,N',N'-tetramethylethylenediamine, 4-dimethylaminopyridine, N-methylimidazole, 1,4-diazabicyclo[2.2.2]octane, 1,8-diazabicyclo[5.4.0]undec-7-ene, etc. Among such examples, triethylamine is particularly preferable. The amount of tertiary amine is preferably 1.0 to 3.0 mol, and more preferably 1.1 to 2.0 mol, per mol of 2,2,2-trifluoro-N-arylacetamide.

Reaction solvents are not limited insofar as they do not react with the reaction ingredients. Specific examples are pentane, hexane, cyclohexane, methylcyclohexane, heptane, octane, and like hydrocarbon solvents; benzene, toluene, xylene, mesitylene, ethylbenzene, chlorobenzene, nitrobenzene, cumene, chlorotoluene, anisole, and like aromatic solvents; diethyl ether, diisopropyl ether, dibutyl ether, t-butyl methyl ether, cyclopentyl methyl ether, dimethoxyethane, tetrahydrofuran, and like ethereal solvents; dichloromethane, chloroform, dichloroethane, dichloropropane, and like halogenated solvents; methyl acetate, ethyl acetate, propyl acetate, butyl acetate, and like ester-based solvents; and acetonitrile and like polar solvents. Among these solvents, polar solvents are preferable, with acetonitrile being particularly preferable. The amount of reaction solvent is preferably 1 to 15 ml, and more preferably 3 to 10 ml, per gram of 2,2,2-trifluoro-N-arylacetamide represented by Formula (1).

The reaction of the present invention is carried out by adding a 2,2,2-trifluoro-N-arylacetamide represented by Formula (1), a tertiary amine, and at least one member selected from the group consisting of phosphorus oxychloride and diphenyl chlorophosphate, to an organic solvent, followed by heating. Excessively low reaction temperatures decelerate the reaction, and excessively high reaction temperatures result in the generation of large amounts of byproducts. Therefore, the reaction temperature is preferably 0 to 150° C., and more preferably 20 to 85° C. The reaction time is preferably 1 to 100 hours, and more preferably 5 to 50 hours.

After the reaction, the solvent is evaporated off to obtain a crude product. Purification by crystallization, recrystallization, distillation, column chromatography, etc., is then performed to obtain an N-aryl-2,2,2-trifluoroacetimidoyl chloride represented by Formula (2).

According to the present invention, N-aryl-2,2,2-trifluoroacetimidoyl chlorides can be safely and efficiently produced.

[Production of 1-aryl-5-(trifluoromethyl)-1H-tetrazoles]

A 1-aryl-5-(trifluoromethyl)-1H-tetrazole represented by Formula (4) can be obtained by reacting an N-aryl-2,2,2-trifluoroacetimidoyl chloride represented by Formula (2) with an azide represented by Formula (3) in the presence of an amine salt in an aromatic hydrocarbon solvent.

"R" in Formulae (2) and (4) is an aryl group optionally having one substituent, and preferably a phenyl or naphthyl group optionally having one substituent. The naphthyl group may be either 1-naphthyl or 2-naphthyl. The position of the substituent is not limited. Examples of the substituent are alkyl groups, alkoxy groups, and halogen atoms.

Such alkyl groups may be linear or branched. When branched, the number and position(s) of branch(es) are not limited. For the reaction to progress smoothly, such an alkyl group preferably has 1 to 10 carbon atoms, and more preferably 1 to 4 carbon atoms. Preferable and specific examples are methyl, ethyl, propyl, isopropyl, n-butyl, isobutyl, s-butyl, t-butyl, and like groups.

The alkyl moiety of such an alkoxy group may be linear or branched. When branched, the number and position(s) of branch(es) are not limited. For the reaction to progress smoothly, the alkyl moiety preferably has 1 to 10 carbon atoms, and more preferably 1 to 4 carbon atoms. Preferable and specific examples of such alkoxy groups are methoxy, ethoxy, n-propoxy, isopropoxy, n-butoxy, but-2-oxy, 2-methylprop-1-oxy, 2-methylprop-2-oxy, and like groups.

Such halogen atoms may be fluorine, chlorine, bromine, or iodine.

Particularly preferable examples of R in Formulae (2) and (4) are phenyl, methylphenyl, methoxyphenyl, fluorophenyl, chlorophenyl, bromophenyl, iodophenyl, and naphthyl groups.

Preferable and specific examples of N-aryl-2,2,2-trifluoroacetimidoyl chlorides are N-phenyl-2,2,2-trifluoroacetimidoyl chloride, N-(2-methylphenyl)-2,2,2-trifluoroacetimidoyl chloride, N-(3-methylphenyl)-2,2,2-trifluoroacetimidoyl chloride, N-(4-methylphenyl)-2,2,2-trifluoroacetimidoyl chloride, N-(2-methoxyphenyl)-2,2,2-trifluoroacetimidoyl chloride, N-(3-methoxyphenyl)-2,2,2-trifluoroacetimidoyl chloride, N-(4-methoxyphenyl)-2,2,2-trifluoroacetimidoyl chloride, N-(2-fluorophenyl)-2,2,2-trifluoroacetimidoyl chloride, N-(3-fluorophenyl)-2,2,2-trifluoroacetimidoyl chloride, N-(4-fluorophenyl)-2,2,2-trifluoroacetimidoyl chloride, N-(2-chlorophenyl)-2,2,2-trifluoroacetimidoyl chloride, N-(3-chlorophenyl)-2,2,2-trifluoroacetimidoyl chloride, N-(4-chlorophenyl)-2,2,2-trifluoroacetimidoyl chloride, N-(2-bromophenyl)-2,2,2-trifluoroacetimidoyl chloride, N-(3-bromophenyl)-2,2,2-trifluoroacetimidoyl chloride, N-(4-bromophenyl)-2,2,2-trifluoroacetimidoyl chloride, N-(2-iodophenyl)-2,2,2-trifluoroacetimidoyl chloride, N-(3-iodophenyl)-2,2,2-trifluoroacetimidoyl chloride, N-(4-iodophenyl)-2,2,2-trifluoroacetimidoyl chloride, N-(naphthalen-1-yl)-2,2,2-trifluoroacetimidoyl chloride, and N-(naphthalen-2-yl)-2,2,2-trifluoroacetimidoyl chloride.

Examples of azides represented by Formula (3) are azides of sodium, potassium, lithium, and like alkali metals; and azides of calcium, magnesium, and like alkaline-earth metals. Alkali metal azides are preferable, with sodium azide being particularly preferable. The amount of azide is preferably 1.0 to 3.0 mol, and more preferably 1.1 to 2.0 mol, per mol of N-aryl-2,2,2-trifluoroacetimidoyl chloride represented by Formula (2).

Amine salts usable in the present invention are formed from amines and acids. Amines include primary, secondary and tertiary amines, and aliphatic amines are particularly preferable. Specific examples of amine salts are, although not limited thereto, methylamine salts, ethylamine salts, propylamine salts, butylamine salts, amylamine salts, hexylamine salts, cyclohexylamine salts, heptylamine salts, octylamine salts, allylamine salts, benzylamine salts, α-phenylethylamine salts, β-phenylethylamine salts, and like primary amine salts; dimethylamine salts, diethylamine salts, dipropylamine salts, dibutylamine salts, diamylamine salts, dihexylamine salts, dicyclohexylamine salts, diallylamine salts, morpholine salts, piperidine salts, hexamethyleneimine salts, and like secondary amine salts; trimethylamine salts, triethylamine salts, tripropylamine salts, tributylamine salts, triamylamine salts, trihexylamine salts, triallylamine salts, pyridine salts, triethanolamine salts, N-methylmorpholine salts, N,N-dimethylcyclohexylamine salts, N,N-dimethylaniline salts, N,N,N',N'-tetramethylethylenediamine salts, 4-dimethylaminopyridine salts, and like tertiary amine salts; etc. Two or more such amine salts may be used in combination. Acids usable herein to form salts are those that usually form salts with amines. Specific examples are, although not limited thereto, hydrochloric acid, hydrogen bromide, sulfuric acid, nitric acid, phosphoric acid, boric acid, hydrogen azide, chloric acid, carbonic acid, hydrogen sulfide, and like inorganic acids; and formic acid, acetic acid, trifluoroacetic acid, propionic acid, oxalic acid, methanesulfonic acid, benzenesulfonic acid, toluenesulfonic acid, and like organic acids. Preferable acids are hydrochloric acid, hydrogen bromide, sulfuric acid, hydrogen azide, acetic acid, and trifluoroacetic acid. Among the aforementioned amine salts formed from amines and acids, triethylamine hydrochloride is particularly preferable. The amount of amine salt is preferably 0.1 to 1.5 mol, and more preferably 0.3 to 1.0 mol, per mol of N-aryl-2,2,2-trifluoroacetimidoyl chloride represented by Formula (2).

Preferable and specific examples of aromatic hydrocarbon solvents usable in the present invention are benzene, toluene, xylene, mesitylene, ethylbenzene, chlorobenzene, nitrobenzene, cumene, chlorotoluene, etc., with toluene and xylene being particularly preferable. Two or more such aromatic hydrocarbon solvents can be used in combination. The amount of solvent is preferably 1 to 15 ml, and more preferably 3 to 10 ml, per gram of N-aryl-2,2,2-trifluoroacetimidoyl chloride represented by Formula (2).

The reaction of the present invention is carried out by adding an N-aryl-2,2,2-trifluoroacetimidoyl chloride represented by Formula (2), an azide represented by Formula (3), and an amine salt to an aromatic hydrocarbon solvent, followed by heating. Excessively low reaction temperatures decelerate the reaction, and excessively high reaction temperatures result in the generation of large amounts of by-products. Therefore, the reaction temperature is preferably 0 to 150° C., and more preferably 50 to 100° C. The reaction time is preferably 5 to 50 hours, and more preferably 12 to 30 hours.

After the reaction, the reaction solution is cooled to room temperature, and then washed with water. The organic phase is then dried, and the solvent is evaporated off to obtain a crude product. Purification by crystallization, recrystallization, column chromatography, etc., is then performed to obtain a 1-aryl-5-(trifluoromethyl)-1H-tetrazole represented by Formula (4).

According to the present invention, 1-aryl-5-(trifluoromethyl)-1H-tetrazoles can be safely and efficiently produced.

BEST MODE FOR CARRYING OUT THE INVENTION

Examples are given below to illustrate the invention in more detail, but the scope of the invention is not limited to these examples.

EXAMPLE 1

N-phenyl-2,2,2-trifluoroacetimidoyl chloride

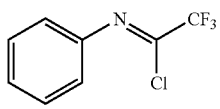

Seven grams (37.0 mmol) of 2,2,2-trifluoro-N-phenylacetamide, 19.84 g (74.0 mol) of diphenyl chlorophosphate, 7.44 g (74.0 mmol) of triethylamine, and 28 ml of acetonitrile were introduced into a 100 ml flask and reacted for 15 hours while being refluxed (82° C.). After the reaction, the reaction solution was cooled to room temperature, 28 ml of ethyl acetate was added thereto, and the precipitate was then filtered off. The filtrate was subjected to solvent removal by evaporation, and the crude product thus obtained was purified by column chromatography (silica gel, ethyl acetate: hexane=3:7), resulting in 6.24 g of N-phenyl-2,2,2-trifluoroacetimidoyl chloride as a yellow liquid (yield: 81.2%).

IR (neat, cm$^{-1}$): 1697, 1489, 1286, 1223, 1196, 1161, 947, 766, 725, 691 $^1$H-NMR (CDCl$_3$): δ 7.41-7.24 (m, 3H), 7.08-7.05 (m, 2H) $^{13}$C-NMR (CDCl$_3$): δ 143.47, 131.94 (q, J=42.8 Hz), 129.12, 127.40, 120.63, 116.86 (q, J=275.8 Hz)

EXAMPLE 2

1-phenyl-5-(trifluoromethyl)-1H-tetrazole

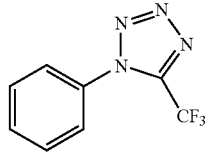

Five grams (24.1 mmol) of N-phenyl-2,2,2-trifluoroacetimidoyl chloride obtained in Example 1, 2.83 g (43.4 mmol) of sodium azide, 1.66 g (12.1 mmol) of triethylamine hydrochloride, and 40 ml of toluene were introduced into a 100 ml flask and reacted at 80° C. for 16.5 hours. After the reaction, the reaction solution was cooled to room temperature and washed with water (30 ml×3). The organic phase was dried over anhydrous magnesium sulfate for 1 hour, filtered, and then subjected to solvent removal by evaporation. The crude product thus obtained was purified by column chromatography (silica gel, ethyl acetate:hexane=3:7), resulting in 4.81 g of 1-phenyl-5-(trifluoromethyl)-1H-tetrazole as a pale yellow oil (yield: 93.2%). IR (neat, cm$^{-1}$): 3071, 1531, 1499, 1312, 1207, 1167, 1013, 766, 691 $^1$H-NMR (CDCl$_3$): δ 7.60-7.54 (m, 3H), 7.38 (d, J=8.7 Hz, 2H), 7.06 (d, J=8.7 Hz, 2H), 3.89 (s, 3H) $^{13}$C-NMR (CDCl$_3$): δ 145.90 (q, J=42.0 Hz), 132.41, 131.59, 131.58, 129.79, 129.76, 125.05, 117.73 (q, J=270.0 Hz) Elemental analysis: Value calculated for C$_8$H$_5$F$_3$N$_4$: C, 44.87%; H, 2.35%; N, 26.16% Value found: C, 44.27%; H, 2.24%; N, 25.95% Decomposition temperature (DSC): 290° C. (1.17 kJ/g), 367° C. (1.55 kJ/g)

EXAMPLE 3

N-(4-methylphenyl)-2,2,2-trifluoroacetimidoyl chloride

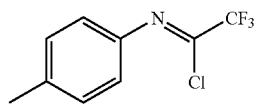

Seven grams (34.5 mmol) of 2,2,2-trifluoro-N-(4-methylphenyl)acetamide, 18.49 g (68.9 mmol) of diphenyl chlorophosphate, 6.97 g (68.9 mmol) of triethylamine, and 35 ml of acetonitrile were introduced into a 100 ml flask and reacted for 18 hours while being refluxed (82° C.). After the reaction, the reaction solution was cooled to room temperature, 25 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 6.77 g of N-(4-methylphenyl)-2,2,2-trifluoroacetimidoyl chloride as a yellow liquid (yield: 88.6%).

IR (neat, cm$^{-1}$): 1684, 1506, 1286, 1223, 1196, 1159, 949, 934, 820 $^1$H-NMR (CDCl$_3$): δ 7.26-7.22 (m, 2H), 7.10-7.04 (m, 2H), 2.39 (s, 3H) $^{13}$C-NMR (CDCl$_3$): δ 140.61, 137.85, 130.55 (q, J=42.8 Hz), 129.69, 121.23, 116.92 (q, J=275.0 Hz), 21.02

EXAMPLE 4

1-(4-methylphenyl)-5-(trifluoromethyl)-1H-tetrazole

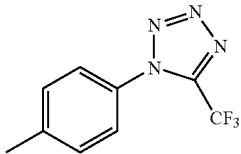

Five grams (22.6 mmol) of N-(4-methylphenyl)-2,2,2-trifluoroacetimidoyl chloride obtained in Example 3, 2.68 g (40.7 mmol) of sodium azide, 1.57 g (11.3 mmol) of triethylamine hydrochloride, and 40 ml of toluene were introduced into a 100 ml flask and reacted at 80° C. for 23 hours. After the reaction, the reaction solution was cooled to room temperature and washed with water (30 ml×3). The organic phase was dried over anhydrous magnesium sulfate for 1 hour, filtered, and then subjected to solvent removal by evaporation. The crude product thus obtained was purified by column chromatography (silica gel, ethyl acetate:hexane=3:7), resulting in 5.01 g of 1-(4-methylphenyl)-5-(trifluoromethyl)-1H-tetrazole as a pale yellow oil (yield: 97.3%).

IR (neat, cm$^{-1}$): 3045, 2930, 1531, 1514, 1312, 1205, 1167, 1034, 1011, 822, 756 $^1$H-NMR (CDCl$_3$): δ 7.37-7.31 (m, 4H), 2.42 (s, 3H) $^{13}$C-NMR (CDCl$_3$): δ 145.96 (q, J=41.2 Hz), 142.28, 130.33, 129.95, 124.83, 117.81 (q, J=270.9 Hz), 21.10 Elemental analysis: Value calculated for C$_9$H$_7$F$_3$N$_4$: C, 47.37%; H, 3.09%; N, 24.98%. Value found: C, 46.89%; H, 2.63%; N, 24.64% Decomposition temperature (DSC): 290° C. (1.09 kJ/g), 360° C. (1.29 kJ/g)

EXAMPLE 5

N-(4-methoxyphenyl)-2,2,2-trifluoroacetimidoyl chloride

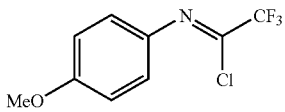

Five grams (22.8 mmol) of 2,2,2-trifluoro-N-(4-methoxyphenyl)acetamide, 12.26 g (45.6 mmol) of diphenyl chlorophosphate, 4.62 g (45.6 mmol) of triethylamine, and 25 ml of acetonitrile were introduced into a 100 ml flask and reacted for 22 hours while being refluxed (82° C.). After the reaction, the reaction solution was cooled to room temperature, 20 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 4.53 g of N-(4-methoxyphenyl)-2,2,2-trifluoroacetimidoyl chloride as a yellow liquid (yield: 83.6%).

IR (neat, cm$^{-1}$): 1676, 1599, 1506, 1285, 1252, 1194, 1159, 1032, 943, 924, 833, 766 $^1$H-NMR (CDCl$_3$): δ 7.26-7.21 (m, 2H), 7.00-6.91 (m, 2H), 3.81 (s, 3H) $^{13}$C-NMR (CDCl$_3$): δ 159.37, 135.25, 127.93 (q, J=42.4 Hz), 124.20, 116.90 (q, J=274.0 Hz), 114.12, 55.45

EXAMPLE 6

N-(4-methoxyphenyl)-2,2,2-trifluoroacetimidoyl chloride

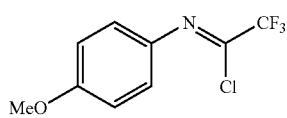

Five grams (22.8 mmol) of 2,2,2-trifluoro-N-(4-methoxyphenyl)acetamide, 7.02 g (45.6 mmol) of phosphorus oxychloride, 4.62 g (45.6 mmol) of triethylamine, and 25 ml of acetonitrile were introduced into a 100 ml flask and reacted for 22 hours while being refluxed (82° C.). After the reaction, the reaction solution was cooled to room temperature, 20 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 4.52 g of N-(4-methoxyphenyl)-2,2,2-trifluoroacetimidoyl chloride as a yellow liquid (yield: 83.4%).

$^1$H-NMR (CDCl$_3$): δ 7.26-7.21 (m, 2H), 7.00-6.91 (m, 2H), 3.81 (s, 3H) $^{13}$C-NMR (CDCl$_3$): δ 159.37, 135.25, 127.93 (q, J=42.4 Hz), 124.20, 116.90 (q, J=274.0 Hz), 114.12, 55.45

EXAMPLE 7

N-(4-methoxyphenyl)-2,2,2-trifluoroacetimidoyl chloride

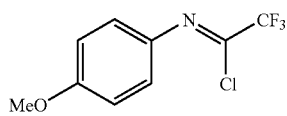

Ten grams (45.6 mmol) of 2,2,2-trifluoro-N-(4-methoxyphenyl)acetamide, 4.92 g (32.0 mmol) of phosphorus oxychloride, 9.23 g (91.2 mmol) of triethylamine, and 50 ml of acetonitrile were introduced into a 200 ml flask and reacted for 19 hours while being refluxed (82° C.). After the reaction, the reaction solution was cooled to room temperature, 30 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 8.94 g of N-(4-methoxyphenyl)-2,2,2-trifluoroacetimidoyl chloride as a yellow liquid (yield: 82.5%).

$^1$H-NMR (CDCl$_3$): δ 7.26-7.21 (m, 2H), 7.00-6.91 (m, 2H), 3.81 (s, 3H) $^{13}$C-NMR (CDCl$_3$): δ 159.37, 135.25, 127.93 (q, J=42.4 Hz), 124.20, 116.90 (q, J=274.0 Hz), 114.12, 55.45

EXAMPLE 8

1-(4-methoxyphenyl)-5-(trifluoromethyl)-1H-tetrazole

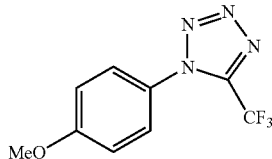

Five grams (21.0 mmol) of N-(4-methoxyphenyl)-2,2,2-trifluoroacetimidoyl chloride obtained in Example 7, 2.46 g (37.8 mmol) of sodium azide, 1.45 g (10.5 mmol) of triethylamine hydrochloride, and 40 ml of toluene were introduced into a 100 ml flask and reacted at 80° C. for 15 hours. After the reaction, the reaction solution was cooled to room temperature and washed with water (30 ml×2). The organic phase was dried over anhydrous magnesium sulfate for 1 hour, filtered, and then subjected to solvent removal by evaporation. The crude product thus obtained was purified by column chromatography (silica gel, ethyl acetate:hexane=3:7), resulting in 5.05 g of 1-(4-methoxyphenyl)-5-(trifluoromethyl)-1H-tetrazole as a pale yellow oil (yield: 98.3%).

IR (neat, cm$^{-1}$): 1609, 1533, 1514, 1466, 1319, 1310, 1259, 1205, 1167, 1111, 1026, 837, 756, 542 $^1$H-NMR (CDCl$_3$): δ 7.38 (d, J=8.7 Hz, 2H), 7.06 (d, J=8.7 Hz, 2H), 3.89 (s, 3H) $^{13}$C-NMR (CDCl$_3$): δ 161.72, 146.03 (q, J=42.1 Hz), 126.51, 124.95, 117.81 (q, J=270.6 Hz), 114.87, 55.72 Elemental analysis: Value calculated for C$_9$H$_7$F$_3$N$_4$O: C, 44.27%; H, 2.89%; N, 22.95% Value found: C, 43.81%; H, 2.81%; N, 22.15%. Decomposition temperature (DSC): 286° C. (1.58 kJ/g), 342° C. (0.64 kJ/g)

EXAMPLE 9

N-(2-methoxyphenyl)-2,2,2-trifluoroacetimidoyl chloride

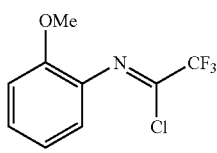

Five grams (22.8 mmol) of 2,2,2-trifluoro-N-(2-methoxyphenyl)acetamide, 12.24 g (45.6 mmol) of diphenyl chlorophosphate, 4.64 g (45.6 mmol) of triethylamine, and 25 ml of acetonitrile were introduced into a 100 ml flask and reacted for 22.5 hours while being refluxed (82° C.). After the reaction, the reaction solution was cooled to room temperature, 20 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 4.55 g of N-(2-methoxyphenyl)-2,2,2-trifluoroacetimidoyl chloride as a yellow liquid (yield: 84.3%).

IR (neat, cm$^{-1}$): 1699, 1595, 1495, 1292, 1252, 1196, 1161, 949, 750 $^1$H-NMR (CDCl$_3$): δ 7.26-7.22 (m, 1H), 7.02-6.91 (m, 3H), 3.85 (s, 3H) $^{13}$C-NMR (CDCl$_3$): δ 149.18, 133.95 (q, J=42.8 Hz), 133.09, 127.94, 120.54, 120.23, 116.81 (q, J=275.0 Hz), 111.78, 55.58

EXAMPLE 10

1-(2-Methoxyphenyl)-5-(trifluoromethyl)-1H-tetrazole

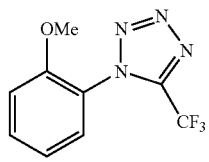

Four grams (16.8 mmol) of N-(2-methoxyphenyl)-2,2,2-trifluoroacetimidoyl chloride obtained in Example 9, 1.98 g (30.2 mmol) of sodium azide, 1.16 g (8.42 mmol) of triethylamine hydrochloride, and 40 ml of toluene were introduced into a 100 ml flask and reacted at 80° C. for 14 hours. After the reaction, the reaction solution was cooled to room temperature and washed with water (30 ml×2). The organic phase was dried over anhydrous magnesium sulfate for 1 hour, filtered, and then subjected to solvent removal by evaporation. The crude product thus obtained was purified by column chromatography (silica gel, ethyl acetate:hexane=3:7), resulting in 4.01 g of 1-(2-methoxyphenyl)-5-(trifluoromethyl)-1H-tetrazole as a pale yellow oil (yield: 97.6%).

IR (neat, cm$^{-1}$): 1601, 1563, 1506, 1470, 1441, 1315, 1288, 1258, 1169, 1124, 1107, 1013, 760, 683 $^1$H-NMR (CDCl$_3$): δ 5 7.59 (ddd, J=7.8, 7.5, 1.7 Hz, 1H), 7.36 (dd, J=7.8, 1.7 Hz, 1H), 7.14-7.08 (m, 2H), 3.79 (s, 3H) $^{13}$C-NMR (CDCl$_3$): δ 153.55, 147.00 (q, J=41.5 Hz), 133.19, 127.22, 121.00, 120.59, 117.60 (q, J=270.4 Hz), 112.07, 55.76 Elemental analysis: Value calculated for C$_9$H$_7$F$_3$N$_4$O: C, 44.27%; H, 2.89%; N, 22.95% Value found: C, 44.35%; H, 3.18%; N, 23.05%. Decomposition temperature (DSC): 283° C. (1.08 kJ/g), 353° C. (0.60 kJ/g)

EXAMPLE 11

N-(4-chlorophenyl)-2,2,2-trifluoroacetimidoyl chloride

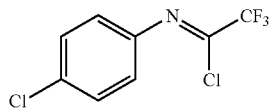

Four grams (17.9 mmol) of 2,2,2-trifluoro-N-(4-chlorophenyl)acetamide, 9.61 g (35.8 mmol) of diphenyl chlorophosphate, 3.62 g (35.8 mmol) of triethylamine, and 20 ml of acetonitrile were introduced into a 50 ml flask and reacted for 16 hours while being refluxed (82° C.). After the reaction, the reaction solution was cooled to room temperature, 16 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 3.40 g of N-(4-chlorophenyl)-2,2,2-trifluoroacetimidoyl chloride as a yellow liquid (yield: 78.6%).

IR (neat, cm$^{-1}$): 1701, 1487, 1286, 1225, 1196, 1163, 1097, 1015, 951, 833, 735 $^{1}$H-NMR (CDCl$_3$): δ 7.42-7.38 (m, 2H), 7.07-6.94 (m, 2H) $^{13}$C-NMR (CDCl$_3$): δ 141.66, 133.28, 132.52 (q, J=42.8 Hz), 129.30, 122.26, 116.75 (q, J=275.0 Hz)

EXAMPLE 12

1-(4-chlorophenyl)-5-(trifluoromethyl)-1H-tetrazole

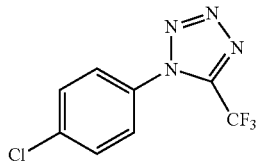

Three grams (12.4 mmol) of N-(4-chlorophenyl)-2,2,2-trifluoroacetimidoyl chloride obtained in Example 11, 1.46 g (22.3 mmol) of sodium azide, 0.85 g (6.20 mmol) of triethylamine hydrochloride, and 30 ml of toluene were introduced into a 100 ml flask and reacted at 80° C. for 24.5 hours. After the reaction, the reaction solution was cooled to room temperature and washed with water (20 ml×2). The organic phase was dried over anhydrous magnesium sulfate for 1 hour, filtered, and then subjected to solvent removal by evaporation. The crude product thus obtained was purified by column chromatography (silica gel, ethyl acetate:hexane=3:7), resulting in 2.84 g of 1-(4-chlorophenyl)-5-(trifluoromethyl)-1H-tetrazole as a pale yellow oil (yield: 92.2%).

IR (neat, cm$^{-1}$): 3101, 1531, 1497, 1313, 1207, 1167, 1096, 1009, 835 $^{1}$H-NMR (CDCl$_3$): δ 6 7.60-7.56 (m, 2H), 7.47-7.43 (m, 2H) $^{13}$C-NMR (CDCl$_3$): δ 146.02 (q, J=42.0 Hz), 138.13, 130.94, 130.25, 126.48, 117.75 (q, J=270.9 Hz) Elemental analysis: Value calculated for C$_8$H$_4$ClF$_3$N$_4$: C, 38.65%; H, 1.62%; N, 22.93%. Value found: C, 38.51%; H, 1.74%; N, 22.40%. Decomposition temperature (DSC): 280° C. (0.97 kJ/g), 368° C. (0.42 kJ/g)

EXAMPLE 13

N-(naphthalen-1-yl)-2,2,2-trifluoroacetimidoyl chloride

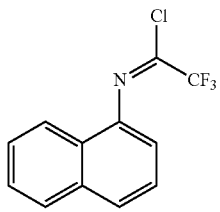

Five grams (20.9 mmol) of 2,2,2-trifluoro-N-(naphthalen-1-yl)acetamide, 11.23 g (41.8 mmol) of diphenyl chlorophosphate, 4.22 g (41.8 mmol) of triethylamine, and 20 ml of acetonitrile were introduced into a 50 ml flask and reacted for 15 hours while being refluxed (82° C.). After the reaction, the reaction solution was cooled to room temperature, 15 ml of ethyl acetate was added thereto, and the precipitate was then filtered off. The filtrate was subjected to solvent removal by evaporation, and the crude product thus obtained was purified by column chromatography (silica gel, ethyl acetate:hexane=3:7), resulting in 4.65 g of N-(naphthalen-1-yl)-2,2,2-trifluoroacetimidoyl chloride as a yellow oil (yield: 86.2%).

IR (neat, cm$^{-1}$): 1686, 1593, 1393, 1286, 1211, 1161, 943, 799, 772, 754, 702 $^{1}$H-NMR (CDCl$_3$): δ 7.89-7.86 (m, 1H), 7.82-7.79 (m, 2H), 7.56-7.48 (m, 3H), 7.18 (d, J=7.4 Hz, 1H) $^{13}$C-NMR (CDCl$_3$): δ 139.67, 133.94, 132.90 (q, J=42.8 Hz), 128.07, 127.65, 126.85, 126.73, 126.23, 125.11, 122.69, 116.9 (q, J=275.0 Hz), 115.07

EXAMPLE 14

1-(naphthalen-1-yl)-5-(trifluoromethyl)-1H-tetrazole

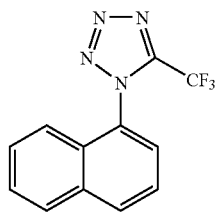

Four grams (15.5 mmol) of N-(naphthalen-1-yl)-2,2,2-trifluoroacetimidoyl chloride obtained in Example 13, 1.84 g (27.9 mmol) of sodium azide, 1.08 g (7.76 mmol) of triethylamine hydrochloride, and 40 ml of toluene were introduced into a 100 ml flask and reacted at 80° C. for 14 hours. After the reaction, the reaction solution was cooled to room temperature and washed with water (30 ml×2). The organic phase was dried over anhydrous magnesium sulfate for 1 hour, filtered, and then subjected to solvent removal by evaporation. The crude product thus obtained was precipitated for 1 hour in 18 ml of n-hexane while being cooled using an ice bath, followed by filtration and drying, thereby giving 3.86 g of 1-(naphthalen-1-yl)-5-(trifluoromethyl)-1H-tetrazole as a white powder (yield: 94.1%).

Melting point: 107.7-108.4° C. IR (KBr, cm$^{-1}$): 3067, 1599, 1531, 1510, 1470, 1448, 1393, 1306, 1215, 1204, 1167, 1153, 1117, 1040, 802, 770, 754, 743, 665 $^{1}$H-NMR (CDCl$_3$): δ 8.11 (d, J=8.3 Hz, 1H) 7.96 (d, J=8.3 Hz, 1H), 7.62-7.50 (m, 4H), 7.02 (d, J=8.3 Hz, 1H) $^{13}$C-NMR (CDCl$_3$): δ 147.68 (q, J=42.0 Hz), 133.91, 132.55, 128.81, 128.73, 128.46, 128.40, 127.64, 125.10, 124.63, 120.74, 117.74 (q, J=270.9 Hz) Elemental analysis: Value calculated for C$_{12}$H$_7$F$_3$N$_4$: C, 54.55%; H, 2.67%; N, 21.21%. Value found: C, 54.27%; H, 2.66%; N, 21.21%. Decomposition temperature (DSC): 272° C. (0.67 kJ/g), 311° C. (0.20 kJ/g)

The invention claimed is:
1. A process for producing an N-aryl-2,2,2-trifluoroacetimidoyl chloride represented by Formula (2):

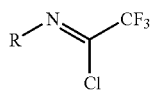

(2)

wherein R is an aryl group optionally having one substituent, the process comprising the step of reacting in an organic solvent a tertiary amine, a 2,2,2-trifluoro-N-arylacetamide represented by Formula (1):

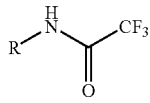
(1)

wherein R is as defined above, and at least one member selected from the group consisting of phosphorus oxychloride and diphenyl chlorophosphate.

2. The process according to claim 1, wherein R is a phenyl, methylphenyl, methoxyphenyl, fluorophenyl, chlorophenyl, bromophenyl, iodophenyl, or naphthyl group.

3. The process according to claim 1, wherein the tertiary amine is triethylamine.

4. A process for producing a 1-aryl-5-(trifluoromethyl)-1H-tetrazole represented by Formula (4):

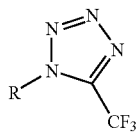
(4)

wherein R is an aryl group optionally having one substituent, the process comprising the step of reacting in an aromatic hydrocarbon solvent, in the presence of an amine salt, an N-aryl-2,2,2-trifluoroacetimidoyl chloride represented by Formula (2):

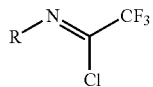
(2)

wherein R is as defined above, and an azide represented by Formula (3):

$M(N_3)_n$ (3)

wherein M is an alkali metal or alkaline-earth metal, and n is 1 or 2.

5. The process according to claim 4, wherein R is a phenyl, methylphenyl, methoxyphenyl, fluorophenyl, chlorophenyl, bromophenyl, iodophenyl, or naphthyl group.

6. The process according to claim 4, wherein the azide is sodium azide.

7. The process according to claim 4, wherein the amine salt is triethylamine hydrochloride.

8. The process according to claim 4, wherein the aromatic hydrocarbon solvent is at least one member selected from the group consisting of toluene and xylene.

* * * * *